United States Patent [19]

Beranek et al.

[11] Patent Number: 4,608,986
[45] Date of Patent: Sep. 2, 1986

[54] PACING LEAD WITH STRAIGHT WIRE CONDUCTORS

[75] Inventors: William J. Beranek, Cooper City; Stanley H. Saulson, Miami, both of Fla.

[73] Assignee: Cordis Corporation, Miami, Fla.

[21] Appl. No.: 656,614

[22] Filed: Oct. 1, 1984

[51] Int. Cl.[4] ............................................. A61N 1/04
[52] U.S. Cl. ................................. 128/786; 128/419 P
[58] Field of Search .................... 128/419 P, 784, 785, 128/786

[56] References Cited

U.S. PATENT DOCUMENTS

| | | | |
|---|---|---|---|
| 3,837,347 | 9/1974 | Tower | 128/785 |
| 3,890,977 | 6/1975 | Wilson | 128/786 |
| 4,365,639 | 12/1982 | Goldreyer | 128/786 |
| 4,386,615 | 6/1983 | Sowton | 128/786 |

*Primary Examiner*—William E. Kamm
*Attorney, Agent, or Firm*—Henry W. Collins; Thomas R. Vigil

[57] ABSTRACT

The pacing lead comprises an elongate lead body which is made of pliable insulation material, which has a generally circular cross-section, which has a proximal end and a distal end and which has at least one lumen therein extending substantially the length thereof. At least one distal electrode or sensor is mounted to the lead body at or adjacent the distal end of the lead body. At least one proximal connector is mounted to the lead body at or adjacent the proximal end of the lead body. At least one uninsulated, relaxed, uncoiled wire conductor is loosely and slidably received in the lumen and is made of a material having a high flexibility and bendability such as of a nickel and titanium alloy. The wire conductor has a diameter less than the diameter of the at least one lumen and is connected at each end, respectively, to the distal electrode and the proximal connector.

17 Claims, 6 Drawing Figures

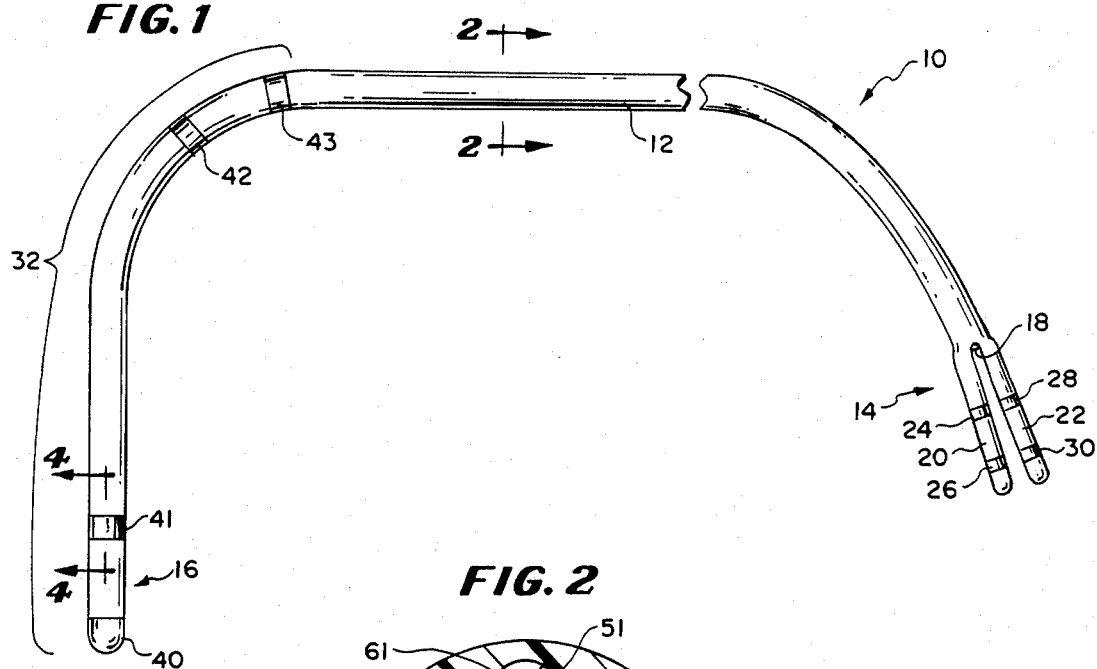
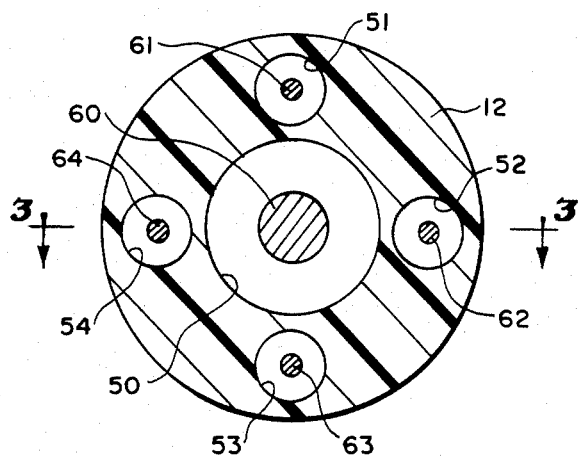
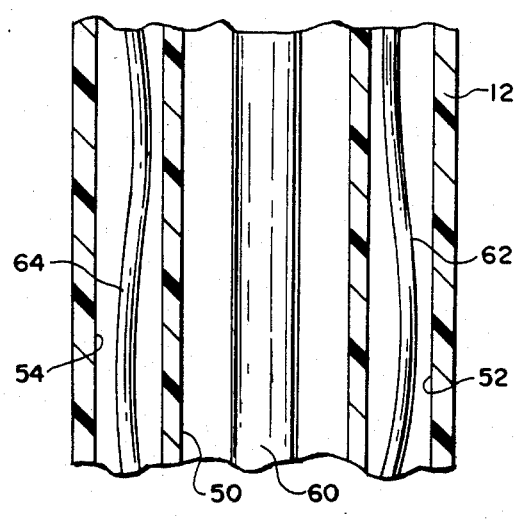
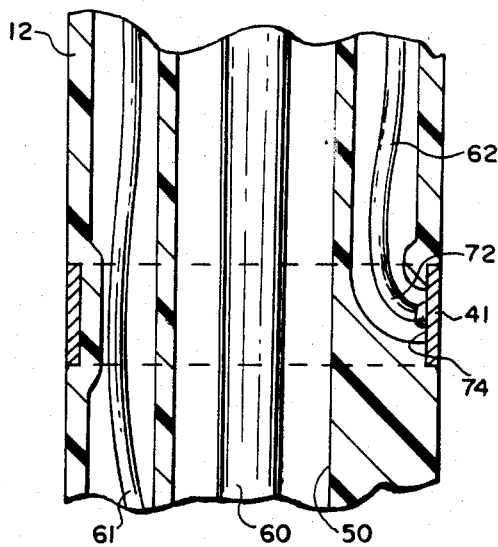

PACING LEAD WITH STRAIGHT WIRE CONDUCTORS

BACKGROUND OF THE INVENTION

1. Field of the Invention

The present invention relates to a pacing lead having straight wire conductors therein and more particularly, to a combination lead body and straight wire conductors which have high flexibility and high bendability and which are mounted within the lead body of the pacing lead in a manner minimizing stress and fatigue on the wire conductors therein.

2. Description of the Prior Art

Heretofore straight wire conductors which are embedded within an insulating material or which have a tightly fitting sleeve or coating of insulating material around the conductor have been proposed for use as pacing leads. However, these prior leads were subject to a high failure rate and were not dependable due to the failure of such leads due to the stress and fatigue placed on the wire conductor as a result of flexing or bending of the insulated wire conductor within the body and particularly, within the heart, upon contractions of the heart.

Examples of some straight wire conductor pacing lead assemblies are disclosed in the Grausz U.S. Pat. No. 3,817,241, the Berkovits U.S. Pat. No. 3,825,015 and the Sable U.S. Pat. No. 3,949,757.

The Grausz U.S. Pat. No. 3,817,241 discloses a straight wire conductor carried by a tubing and embedded in the wall of the tubing so that it is electrically insulated from the interior walls and exterior walls of the tubing.

The Sable U.S. Pat. No. 3,949 757 discloses a catheter for atrio-ventricular pacing which includes one straight wire conductor embedded in an oval-in-cross-section lead body and an insulated straight wire conductor received in a larger-in-diameter lumen in the lead body.

The Berkovits U.S. Pat. No. 3,825,015 discloses a plurality of straight insulated wire conductors within the hollow interior of a catheter.

Some other medical electronic devices for uses other than long term pacing (30 days or longer) which utilize straight wire conductors previously have been proposed. See for example, the Kline U.S. Pat. No. 4,172,451.

As a result of their high failure rate, straight wire conductors have not been widely used in pacing leads. Instead coiled wire conductors have been used since a coil is able to withstand a greater number of flexes or bends within the human body, such as caused by contractions of the heart, without any failures, cracking or breaking of the wire conductor occuring over the expected life of the pacing lead.

A disadvantage, however, of using a coiled conductor is that the wire conductor must have a sufficient diameter to provide the coiled wire conductor with sufficient strength to withstand flexing or bending thereof and to provide the coiled wire conductor with sufficient conductivity for the conduction of electric current therethrough. Also the lumen defined within the coiled wire conductor must be large enough to receive a stiffening stylet therein.

Furthermore, in a bipolar lead one coiled wire conductor is surrounded by a sheath, sleeve or tube of insulating material and a second outer coiled wire conductor is received around that sheath and then has an outer sheath, sleeve or tube of insulating material therearound. This results in a pacing lead body which has a significant thickness.

It will be appreciated that it is desirable to have a minimal thickness of the lead body in view of the limitations placed on the thickness of the lead body by the inner diameter of the blood vessels through which the lead body will be inserted to reach a heart chamber. Typically the diameter of a lead body is approximately 0.050 inch for a unipolar lead having one coiled conductor and one tip electrode and approximately 0.082 inch for a bipolar lead having two coiled conductors and two electrodes at the distal end of the lead.

It also will be appreciated that the greater the diameter of the lead body, the greater its impedance to the flow of blood through a blood vessel and the more rigid the lead will be, rendering it more prone to breakage.

As will be described in greater detail hereinafter, the pacing lead of the present invention provides a pacing lead body of minimal thickness or diameter and containing one or more straight wire conductors which are constructed and arranged so as not to have the high failure rate of the earlier straight wire conductor pacing leads and which have the advantages of the earlier straight wire pacing leads of a minimal outer diameter or thickness which is less than, or not greater than, the thickness of current pacing leads having coiled conductors therein. This is achieved by providing the lead body with a lumen for receiving each wire conductor that has a greater diameter than the wire conductor received therein so that an uninsulated, relaxed, uncoiled wire conductor can be loosely and slidably received within the lumen of the lead body. Also each wire conductor is made of a material which has high flexibility and bendability. One such type of material is a memory effect alloy, such as the equiatomic nickel-titanium alloy. These alloys have an austenite-martensite transformation. In the high temperature or austenite phase, the material exhibits a standard stress-strain curve and exhibits a unique stress-strain curve for the same alloy in its martensitic state. This unique curve exhibits a low strength yield point which represents the re-orientation of the martensitic plates, but does not introduce any work hardening or other degradations to the mechanical fatigue life. The strain induced is recoverable and as long as the device is stressed at a strain, less than the limit designated by a point on the unique curve, no loss of fatigue life is observed. In this application, an equiatomic alloy of nickel and titanium is used. Additions of other elements such as cobalt or vanadium are used to vary the transition temperature between the austenite and martensite phase.

Heretofore such a lead has not been proposed. However, the use of a titanium-nickel alloy rod in a catheter for giving it a curved shape has been proposed in the Wilson U.S. Pat. No. 3,890,977.

SUMMARY OF THE INVENTION

According to the present invention there is provided a pacing lead comprising an elongate lead body which is made of pliable insulation material, which has a compact cross-section, which has a proximal end and a distal end and which has at least one lumen therein extending substantially the length thereof, at least one distal electrode or sensor at or adjacent said distal end of said lead body, at least one proximal connector at or adjacent said proximal end of said lead body, and at least one uninsulated, relaxed, uncoiled wire conductor which is made of a material having a high flexibility and bendability, which has a diameter less than the diameter of said at least one lumen, which is loosely and slidably received in said lumen, and which is connected at each end, respectively, to said distal electrode and said proximal connector.

Preferably, the wire conductor is made of an alloy of nickel and titanium.

BRIEF DESCRIPTION OF THE DRAWINGS

FIG. 1 is a plan view of an atrio-ventricular pacing lead with straight wire conductors therein constructed in accordance with the teachings of the present invention.

FIG. 2 is a sectional view of the lead body and is taken along line 2—2 of FIG. 1.

FIG. 3 is a fragmentary axial sectional view of the pacing lead shown in FIGS. 1 and 2 and is taken along line 3—3 of FIG. 2.

FIG. 4 is a fragmentary axial sectional view of the pacing lead shown in FIG. 1 and is taken along line 4—4 of FIG. 1.

DESCRIPTION OF THE PREFERRED EMBODIMENT

Figure 5:
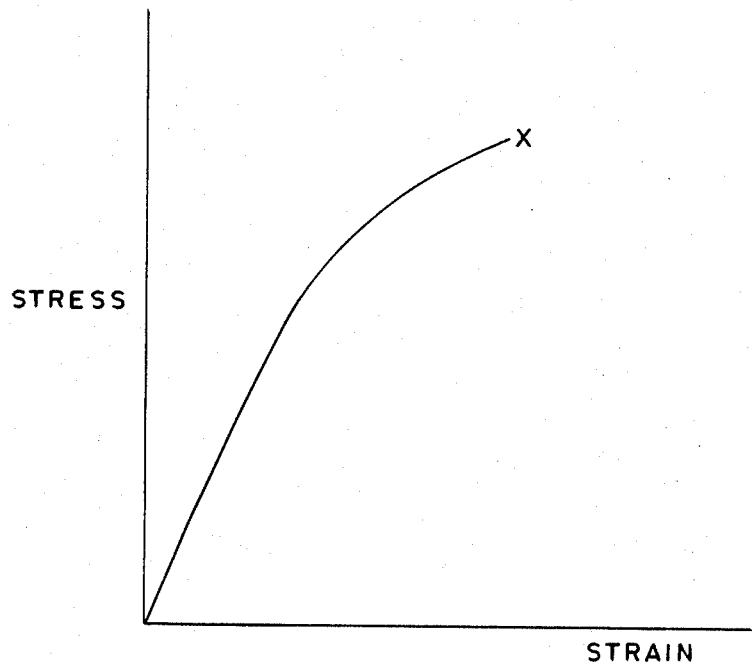
FIG. 5 is a stress-strain curve for the equiatomic nickel-titanium alloy in high temperature austenite phase.

Referring now to FIG. 1 in greater detail there is illustrated therein an atrio-ventricular dual chamber pacing lead 10 which is constructed in accordance with the teachings of the present invention. The pacing lead 10 has a lead body 12 having a proximal end 14 and a distal end 16. At the proximal end 14 there is provided a stylet receiving opening 18 and two connector fingers 20 and 22 which are formed integral with or connected to the proximal end 14 of the pacing lead 10. Each connector finger 20 or 22 has two spaced apart connector rings or sleeves 24, 26 or 28, 30 thereon.

Distal end portion 32 of the pacing lead 10 has four electrodes 40–43 which comprise a first tip electrode 40, a first ring electrode 41 positioned about the lead body and spaced behind the tip electrode 40 approximately 2.5 cm, a second ring electrode 42 on the lead body 12 spaced approximately 10 cm behind the first ring electrode 41 and a third ring electrode 43 on the lead body 12 and spaced approximately 2.5 cm behind the second ring electrode 42 in the distal end portion 32 of the lead body 12.

Referring now to FIG. 2, the lead body 12 is circular in cross section and is made of a soft pliable material such as polyurethane or similar biocompatible polymer.

The lead body has a larger in diameter central lumen 50 and four wire conductor receiving smaller lumina 51–54 which are equally spaced from each other about the central lumen 50. The lead body 12 with the five lumina 50–54 therein can be formed by extrusion of polyurethane over an air mandrel so as to provide five lumina. Alternatively, the lead body 12 can be formed by extrusion of the polyurethane polymer over mandrel wires, by the dipping of mandrel wires in polymer or by molding the lead body 12 in a five pin mold.

The electrodes 40–43 are constructed of a metal such as platinum-iridium, stainless steel, titanium, tantalum, a scintered metal, a porous elgiloy or carbon material.

In accordance with the teachings of the present invention, the central lumen 50 is sized to receive a stylet 60 therein as shown within the lead body 12 in FIGS. 2, 3 and 4. Such a stylet 60 of course, is only used for stiffening of the lead 10 and would be removed once the distal end portion 32 of the pacing lead 10 has been properly positioned within the ventricle or atrium of a heart.

Further, in accordance with the teachings of the present invention, the pacing lead 10 includes four, uninsulated, straight, relaxed, uncoiled wire conductors 61–64 each of which is received in respective ones of the lumens 51–54. To minimize stress and fatigue on the wire conductors, the wire conductors 61–64 are loosely and slidably received in each of the respective lumens 51–54. For this purpose, each lumen 51–54 has a diameter greater than the diameter of each of the wire conductors 61–64. For example, each wire conductor 61–64 preferably has a diameter of approximately 0.005 inch and each of the lumens 51–54 has a diameter of approximately 0.007 to 0.009 inch.

Still further, in accordance with the teachings of the present invention, each of the wire conductors 61–64 is made of a conductive metal which has the characteristic of being highly flexible and highly bendable without breaking. Some materials which exhibit these characteristics are equiatomic alloys of nickel and titanium with substitutional alloys added in replacement for the nickel, such as cobalt or vanadium. The generic name for these alloys is Nitinol, which stands for Nickel-Titanium-Naval Ordinance Laboratory, where they were first developed. One preferred composition of Nitinol has approximately equal parts of nickel and titanium with traces of either cobalt or vanadium. A straight wire made from this alloy will be typically stiff but flexible at temperatures above 110° F. (the stress strain curve is represented by that shown in FIG. 5). Below the martensitic transformation temperature, which in this case is represented as 110° F., the material will be soft and pliable and will follow the unique stress strain curve shown in FIG. 6.

Figure 6:
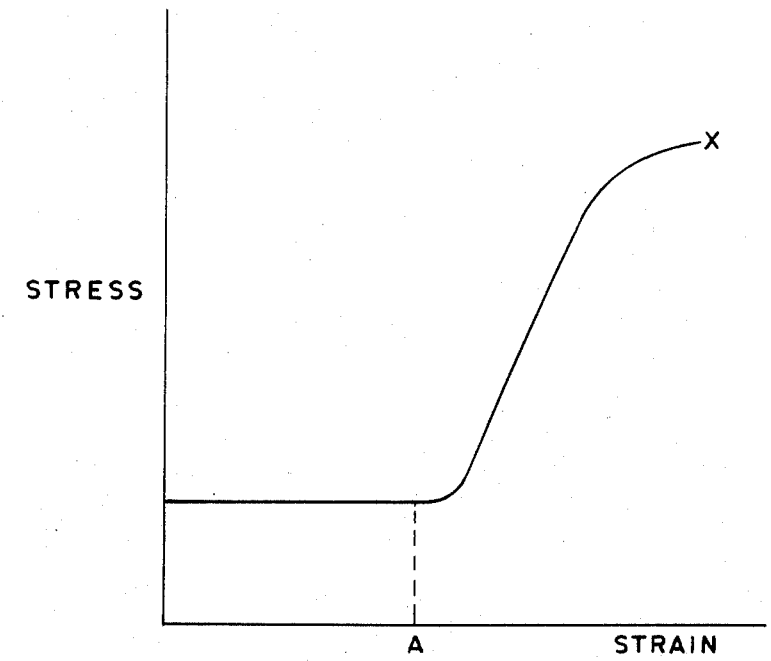
FIG. 6 is a unique stress-strain curve for the same alloy in its martensitic state.

The unique curve shown in FIG. 6 exhibits a low strength yield point which represents the re-orientation of the martensitic plates, but does not introduce any work hardening or other degradations to the mechanical fatigue life. The strain induced is recoverable and as long as the device is stressed at a strain, less than the limit, designated by a point A shown in the graph of FIG. 6, no loss of fatigue life is observed. In this application, an equiatomic alloy of nickel and titanium is used. Additions of other elements such as cobalt or vanadium are used to vary the transition temperature between the austenite and martensite phase.

The pliability or bendability of each wire conductor 61–64 made from this material plus the loose and slidable mounting of each wire conductor 61–64 in one of the lumina 51–54 minimizes the stress and fatigue placed on the wire conductors 61–64 and greatly enhances the life of the pacing lead 10 having such wire conductors 61–64 mounted therein.

In the illustrated embodiment and as shown in FIG. 4, a distal end 72 of one wire conductor 62 is shown welded or soldered to an inner surface 74 of the first ring electrode 41. It is to be understood that alternative methods for connecting the distal end 72 of the wire conductor 62 to the ring electrode 41 can be employed such as bringing the distal end 72 of the wire conductor 62 out through an opening in the lead body 12 and around the lead body 12 and then mounting the ring electrode 41 thereover, as is common in the field of pacing leads.

Similarly, the wire conductor 61 is connected to the tip electrode in a conventional manner.

It is to be understood that the lead body 12 can have more or less than five lumina, 50-54. For example, a unipolar lead could be constructed with one wire conductor receiving lumen and one stylet receiving lumen. Alternatively, a bi-polar lead could be provided with or without the stylet receiving lumen and with two wire conductor receiving lumina.

Additionally, one or more of the electrodes 40-43 can be replaced by a physiological sensor such as an oxygen sensor. Such a sensor can be of the type disclosed in the Wirtzfeld U.S. Pat. No. 4,202,339.

Finally, the electrodes 40-43 at the distal end 16 of the lead body 12 can be separate electrode structures, like fingers, with two of the electrode structures being sutured onto the surface of the atrium and two of the electrode structures being sutured onto the surface of the ventricle.

It is contemplated that by utilizing the teachings of the present invention, a pacing lead 10 can be provided which has anywhere from one to eight or more straight wire conductors therein. Also, for a unipolar lead with only one wire conductor receiving lumen and one straight wire conductor, the outer diameter of the lead can be as small as 0.02 inch.

To increase the safety factor of the lead 10, it may be desirable to connect two of the wire conductors 61-64 to each electrode 40, 41, 42 or 43 and to the corresponding proximal connector to provide two conductive paths in the highly unlikely event of one wire conductor breaking after being flexed a large number of times.

It is to be noted that presently used pacing leads having one or more coiled conductors therein and utilize a metal sold under the trademark Elgiloy which has a resistance that is much less than the resistance of Nitinol. Typically Nitinol has a resistance eight times that of Elgiloy TM. However, the overall resistance of a generally straight Nitinol wire is approximately the same as that of the longer coiled Elgiloy TM wire conductor so that there is no sacrifice in conductivity using straight wire conductors while there is a gain in flexibility and reduction of lead diameter. In this respect, the outer diameter of the lead body 12 is between approximately 0.052 and 0.055 inch and preferably approximately 0.053 inch.

From the foregoing description, it will be apparent that the pacing lead 10 of the present invention has a number of advantages, some of which have been described above and others of which are inherent in the invention.

Also, modifications can be made to the pacing lead 10 of the present invention without departing from the teachings of the present invention.

In this respect and as stated above, anywhere from one to nine or more lumina can be provided in the lead body 12 and one to eight or more straight wire conductors can be loosely and slidably received in each of the lumina.

Also, redundancy can be provided by connecting two wire conductors between a distal electrode and a proximal connector.

Additionally, straight wire or rod shaped proximal terminal connectors can be employed in place of rings 24, 26, 28 and 30 and fingers 20 and 22.

Further, the pacing lead 10 can be provided with a number of electrodes and used for cardiac mapping, i.e., the mapping of endocardial conduction pathways for locating a focus whose conduction rate is greater than normal, instead of for pacing.

Thus, a number of modifications can be made to the pacing lead of the present invention without departing from the teachings of the invention. Accordingly, the scope of the invention is only to be limited as necessitated by the accompanying claims.

I claim:

1. A multielectrode pacing lead which is implantable in a heart for long term pacing of the heart, comprising an elongate continuous, solid core lead body which is made of a pliable insulation material, which has a compact cross-section, which has a proximal end and a distal end, and which is multiluminal, having a central lumen adapted to receive a stylet therein and at least four conductor-receiving lumina therein, in planetary arrangement relative to said central lumen, extending the length thereof, a plurality of distal electrodes or sensors at or adjacent said distal end of said lead body, at least one proximal connector at or adjacent said proximal end of said lead body, and at least four uninsulated, relaxed, uncoiled, generally straight wire conductors which are made of an equiatomic alloy of nickel and titanium which, at the temperature of a human body is substantially more flexible and bendable than wire conductors made of other metals, each uninsulated wire conductor having a diameter less than the diameter of said lumen in which it is received, each conductor being loosely and slidably received in said associated lumen, and being connected at each end, respectively, to one of said distal electrodes or sensors and said proximal connector, and said lead body having a diameter no greater than 0.055 inch.

2. The pacing lead of claim 1 wherein said wire conductor is made of an equiatomic alloy of titanium and nickel with a trace of vanadium.

3. The pacing lead of claim 1 wherein said wire conductor alloy comprises an equiatomic alloy of nickel and titanium with a trace of cobalt.

4. The pacing lead of claim 1 wherein said nickel titanium wire conductor is substantially straight, is stiff but flexible at temperatures above 110° F., and is soft and pliable at temperatures below 110° F.

5. The pacing lead of claim 1 wherein said lead body is made of a solid core of soft, pliable polyurethane material.

6. The pacing lead of claim 1 wherein said lead body has a generally circular cross-section and an outer diameter of between approximately 0.02 and 0.06 inch.

7. The pacing lead of claim 1 wherein each conductor-receiving lumen has a diameter of between 0.007 and 0.009 inch and each wire conductor has a diameter of approximately 0.005 inch.

8. The pacing lead of claim 1 wherein said conductor-receiving lumina each have a diameter of between 0.007 and 0.009 inch and said central lumen has a diameter of approximately 0.018 inch.

9. The pacing lead of claim 1 including second, third and fourth distal electrodes and second, third and fourth proximal connectors located respectively adjacent the distal and proximal ends of said lead body, said wire conductors being loosely and slidably received in said conductor-receiving lumina and each being connected at its respective ends to one of said distal electrodes and one of said proximal connectors.

10. The pacing lead of claim 1 wherein said outer diameter of said lead body is between approximately 0.052 inch and 0.055 inch.

11. The pacing lead of claim 10 wherein said outer diameter of said lead body is approximately 0.053 inch.

12. The pacing lead of claim 10 wherein said fourth central lumen has a diameter of approximately 0.018 inch.

13. The pacing lead of claim 10 wherein said first, second, third and fourth lumina are equally spaced from each other within said lead body about said fifth central lumen and each lumen has a diameter of approximately 0.007 to 0.009 inch and each wire conductor has a diameter of approximately 0.005 inch.

14. The pacing lead of claim 10 wherein said first named electrode is a tip electrode and said second, third and fourth electrodes are first, second and third ring electrodes.

15. The pacing lead of claim 14 wherein said first ring electrode is positioned on said lead body approximately 2.5 cm behind said tip electrode, said second ring electrode is positioned on said lead body approximately 10 cm behind said first ring electrode, and said third ring electrode is positioned on said lead body approximately 2.5 cm behind said second electrode.

16. The pacing lead of claim 10 wherein said proximal end of said lead body has a stylet receiving opening and two finger shaped connector portions, each connector portion of said lead body having two connectors thereon.

17. The pacing lead of claim 16 wherein said two connectors on each finger portion are connector rings spaced apart from each other and positioned on one of said finger portions.

* * * * *